United States Patent [19]

Jordan

[11] 4,087,475

[45] May 2, 1978

[54] CARBONYL FLUORINATION PROCESS

[76] Inventor: Robert Kenneth Jordan, 3979 Tuxey Ave., Pittsburgh, Pa. 15227

[21] Appl. No.: 592,760

[22] Filed: Jul. 3, 1975

[51] Int. Cl.$^2$ .................... C07C 19/08; C07C 21/18
[52] U.S. Cl. ........................ 260/653; 260/611 R; 260/653.3; 560/1
[58] Field of Search ................... 260/653, 653.3

[56] References Cited
PUBLICATIONS

Hudlicky et al., Chemistry of Organic Fluorine Compounds, p. 112 (1962).
Traube et al., Ber. Devt. Chem. 52B 1272-1284 and 1293-1298 (1919).

*Primary Examiner*—C. Davis

[57] ABSTRACT

A process for the production of fluorinated organic compounds wherein a carbonyl containing organic compound and adducts of sulfur trioxide or sulfur dioxide with metal fluorides are combined.

1 Claim, No Drawings

CARBONYL FLUORINATION PROCESS

This invention relates to a process for the production of fluorinated compounds containing two fluorine atoms on a single carbon atom and on adjacent carbon atoms by combining a carbonyl or epoxide containing organic compound with a metal fluorosulfonate, metal fluoride fluorosulfonate, metal fluorosulfinite or metal fluoride fluorosulfinite.

Organic fluorides are especially difficult to make, usually requiring highly corrosive systems which are difficult to handle. An example is dichlorodifluoromethane which is made by reacting carbon tetrachloride with hydrogen fluoride over a catalyst which results in an atmosphere containing hydrogen fluoride, hydrogen chloride and often other undesirable compounds. As dichlorodifluoromethane is especially useful as a propellant for aerosols and as a foaming agent for flexible and rigid polyurethane foams, an economic and simple means for its production is highly desirable. Vinyl fluoride can be made by the addition of hydrogen fluoride to acetylene over a catalyst and used as a monomer in the production of films that are resistant to degradation by light and by the elements. Tetrafluoroethylene can be made by several processes, some necessitating the use of elemental fluorine which is very expensive. Tetrafluoroethylene is used as a non-stick coating intermediate for pots, pans and even snow shovels, the actual coating being polymerized tetrafluoroethylene.

Therefore, it is an object of my invention to provide a new and improved process for the production of fluorinated organic compounds.

It is another object to provide a new and improved process for the production of dichlorodifluoromethane.

It is another object to provide a new and improved process for the production of fluorinated ethers.

My invention is a process for the production of fluorinated organic compounds wherein an organic carbonyl containing compound and at least one of metal fluorosulfonates, metal fluoride fluorosulfonates, metal fluorosulfinites and metal fluoride fluorosulfinites are combined at a temperature in the range of from about $-50°$ C to about 500° C.

I have unexpectedly discovered that carbonyl compounds such as carbon monoxide, acetaldehyde, acetone and diethyl oxalate are fluorinated with varying degrees of difficulty by combining them with metal fluorosulfonates and metal fluorosulfinites, and especially facilely using metal fluoride fluorosulfonate and metal fluoride fluorosulfinites. The preferred metal fluoride-sulfur trioxide adducts are metal fluoride fluorosulfonates. Thus sulfur trioxide is readily added to fluorspar at about 100° C at about 5 atmospheres to almost quantitatively yield calcium fluorosulfonate;

$$CaF_2 + 2 SO_3 \rightarrow Ca(SO_3F)_2$$

And when the calcium fluorosulfonate is heated to about 200° C and acetaldehyde passed through it, 1,1-difluoroethane is found in the product gas stream. When acetone is used, 2,2-difluoropropane is found.

As noted, calcium fluorosulfonate is formed by the consumption of two moles sulfur trioxide per mole of fluorspar. When the compound is heated to about 250° C, sulfur trioxide is evolved with the formation of calcium fluoride fluorosulfonate;

$$Ca(SO_3F)_2 \rightarrow CaF(SO_3F) + SO_3$$

It turns out besides being more economical, the compound also combines more efficiently with compounds containing carbonyl groups. When heated to somewhat over 300° C and carbon monoxide passed over the gas stream is found to have converted to the extent of about 15 percent and tetrafluoroethylene and its polymers are the only products found in the system. Ferric fluoride monofluorosulfonate is even more reactive, it having the composition $FeF_2(SO_3F)$. Potassium fluorosulfonate is less effective because of its low melting point evidentally, forming a sticky looking mass.

The fluorosulfonates are preferred over metal fluorosulfinites because they are more stable at high temperatures, for example potassium fluorosulfonate is stable at even above 200° C while potassium fluorosulfinite, made by the addition of sulfur dioxide to potassium fluoride, begins to decompose at even 100° C. Yet depending on the activity of the carbonyl containing compound, the process can often be conducted with active metal fluoride adducts with either of sulfur dioxide or sulfur trioxide. Thus, ferrous fluoride fluorosulfonate, $FeF(SO_3F)$, and cyclohexanone at 75° C gives 1,1-difluorocyclohexane. The analogous ferrous fluoride fluorosulfinite, $FeF(SO_2F)$, yields the identical product but ideally in the presence of activating compounds, for example ethers.

Finally, diketene was decomposed to ketene which was passed over calcium fluoride fluorosulfonate at somewhat above 300° C to give about a 30 percent conversion to vinylidene fluoride,, a useful monomer in the production of polyvinylidene fluoride, a slippery plastic used for low load plastic bearings and other molded plastic parts. Diketene and ferrous fluoride fluorosulfonate in a one to one mole ratio gave about 70 percent conversion of the contained carbonyl group and the major product was found to be the corresponding difluorocyclic ether.

A sample of 0.2 g ethylene-carbon monoxide copolymer containing about 45 percent carbon monoxide in the form of a polyketone of very high molecular weight (via gamma ray polymerization at Brookhaven National Laboratory, Upton, N.Y.) as a powder was intimately mixed with about one gram of ferrous fluoride fluorosulfonate powder and rapidly heated to just over 300° C and held there for an hour before being dumped into 30 ml cold water. A brownish white solid was obtained which on spectral analysis showed the presence of carbon-fluorine bonds, especially $-CF_2-$, which should be especially useful in the form of molded objects or films because of the slippery surface.

The range of fluorosulfonates and fluorosulfinites useful in process and described more fully in my co-pending application Ser. No. 411,487 filed Oct. 31, 1973 and it is preferred that these are made by the addition of the sulfur oxide to the metal fluoride. Further, it is ideal to use metal fluoride fluorosulfonates, for examples calcium fluoride fluorosulfonate and ferric difluoride fluorosulfonate, because they require less sulfur oxide and generally are more stable thermally. Thus calcium fluoride fluorosulfonate is stable to above 300° C, and in fact at short residence times to above 400° C. This is especially important to the fluorination of carbon monoxide which takes place at such higher temperatures simply by passing the gas through a bed of calcium fluoride fluorosulfonate, ideally the carbon monoxide being preheated at about 350°–400° C. The almost exclusive product is tetrafluoroethylene, probably by a two step mechanism wherein the initial product is the radical difluorocarbene, $$CO + CaF(SO_3F) \rightarrow CaSO_4 + CF_2:$$

and then two radicals combine to form tetrafluoroethylene.

$$2 CF_2: \rightarrow CF_2::CF_2$$

According to the provision of the patent statutes, I have explained the principle of my invention and have illustrated and described what I now consider to represent its best embodiment. However, I desire to have it understood that within the scope of the appended claims, the invention may be practiced otherwise.

I claim:

1. A process for the production of substituted difluoromethylene compounds comprising combining a carbonyl selected from carbon monoxide, carbonyl halides, aldehydes and ketones with at least one of metal fluorosulfonates, metal fluoride fluorosulfonates, metal fluorosulfinites and metal fluoride fluorosulfinites at a temperature in the range of about −50° C to 500° C.

* * * * *